United States Patent [19]

Sprecker et al.

[11] Patent Number: 5,378,685
[45] Date of Patent: Jan. 3, 1995

[54] PROCESS FOR PREPARING MIXTURE OF TRIMETHYL AND DIMETHYLMETHYLENE PROPYL POLYHYDROPYRANS, PRODUCTS PRODUCED THEREBY PERFUMERY USES OF SUCH PRODUCT

[75] Inventors: Mark A. Sprecker, Sea Bright; Robert P. Belko, Woodbridge; Marie R. Hanna, Keyport, all of N.J.

[73] Assignee: International Flavors & Fragrances Inc., New York, N.Y.

[21] Appl. No.: 214,185

[22] Filed: Mar. 17, 1994

[51] Int. Cl.$^6$ .............................................. A61K 7/46
[52] U.S. Cl. ..................................... 512/11; 549/356; 549/416
[58] Field of Search .................... 512/11; 549/356, 416

[56] References Cited

U.S. PATENT DOCUMENTS

| | | | |
|---|---|---|---|
| 2,422,648 | 6/1947 | Williams et al. | 512/11 |
| 3,252,998 | 5/1966 | Ohloff et al. | 549/356 |
| 3,455,957 | 7/1969 | Cahn et al. | 549/356 |
| 3,681,263 | 8/1972 | Van der Linde | 512/11 |
| 4,192,782 | 3/1980 | Hall et al. | 252/522 R |
| 4,962,090 | 10/1990 | Sprecker et al. | 549/416 |
| 5,162,551 | 11/1992 | Broekhof et al. | 549/356 |

OTHER PUBLICATIONS

Gramenitskaya, et al, Zh. Org. Khim., 1975, 11(5), pp. 990–995 (abstracted at Chem. Abstracts) vol. 83, 1975, Abstract No. 58767k.
Hinnen, et al, Bull. Soc. Chim. France 1964(7), pp. 1492–1498 (abstracted at Chem. Abstracts) vol. 61, No. 10648c–h.
Williams, et al, (II), J. Am. Chem. Soc. 72, pp. 5738–5743, (1950), title "A Synthesis of Substituted Pyrans".

*Primary Examiner*—James H. Reamer
*Attorney, Agent, or Firm*—Arthur L. Liberman

[57] ABSTRACT

Described is a process for preparing trimethyl and dimethylmethylene propyl polyhydropyran derivatives including compounds defined according to the structure:

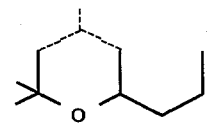

which defines a mixture wherein in the mixture, in each of the compounds one of the dashed lines is a carbon-carbon double bond and each of the other of the dashed lines represents a carbon-carbon single bond as well as the compound having the structure:

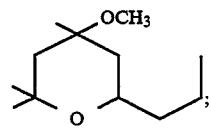

products produced thereby; perfumery uses of such products; process intermediates of such process including compounds defined according to the structures:

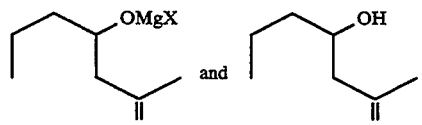

wherein X represents chloro or bromo.

12 Claims, 6 Drawing Sheets

GLC PROFILE FOR EXAMPLE I

GLC PROFILE FOR EXAMPLE II

FIG. 5 NMR SPECTRUM FOR EXAMPLE II, FRACTION 15 DISTILLATION

PROCESS FOR PREPARING MIXTURE OF TRIMETHYL AND DIMETHYLMETHYLENE PROPYL POLYHYDROPYRANS, PRODUCTS PRODUCED THEREBY PERFUMERY USES OF SUCH PRODUCT

BACKGROUND OF THE INVENTION

Our invention relates to trimethyl and dimethylmethylene propyl polyhydropyran derivatives and processes for preparing mixtures of trimethyl and dimethylmethylene propyl polyhydropyrans as well as perfumery uses of such trimethyl and dimethylmethylene propyl polyhydropyran derivatives and process intermediates for such process including the compounds having the structures:

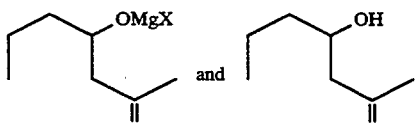

wherein X is chloro or bromo.

There has been considerable work performed relating to substances which can be used to impart (or enhance) fragrances to (or in) various consumable materials including perfume compositions, colognes and perfumed articles such as solid or liquid anionic, cationic, nonionic or zwitterionic detergents, fabric softeners and cosmetic powders. These substances are used to diminish natural materials some of which may be in short supply and to provide more uniform properties in the finished product.

Winey, chamomile, juniper, sage, citrusy, spicy, pineapple, green and floral aromas with natural rose, tobacco-like and animalic undertones are particularly desirable in perfume compositions.

Chemical compounds having the pyran ring are known to be useful in flavor and fragrance compositions. Thus, published Japanese Application 74/011073 (Mar. 14, 1974) Mitsui Toatsu Chemicals Inc. discloses 2,5 diethyl tetrahydropyran-containing perfumes having rose-like aromas and good stability in air, sunlight and humidity.

U.S. Pat. No. 2,422,648 at column 5, lines 34–55 states:

"The unsaturated cyclic ethers prepared by the process of the invention are useful as diluents, modifying agents, and processing reagents in the textile industry, and the higher members particularly are valuable as solvents. They may also be used as reagents and/or additives in the formation of synthetic resins, plastics and synthetic rubbers and the higher members may serve as insecticides, fungicides, parasiticides or as constituents of insecticidal, fungicidal and parasiticidal compositions, etc. In addition, they are valuable intermediates in the syntheses of valuable organic products; for example, the substituted dihydropyrans may be hydrogenated, if desired, in the presence of a suitable hydrogenation catalyst such as Raney nickel, to produce a novel substituted tetrahydropyran compounds having the formula:

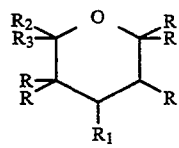

(wherein the R's represent hydrogen or non-olefinic hydrocarbon)."

Williams, et al, J. Am. Chem. Soc., 72, 5738–43 (1950) sets forth the following reaction sequence:

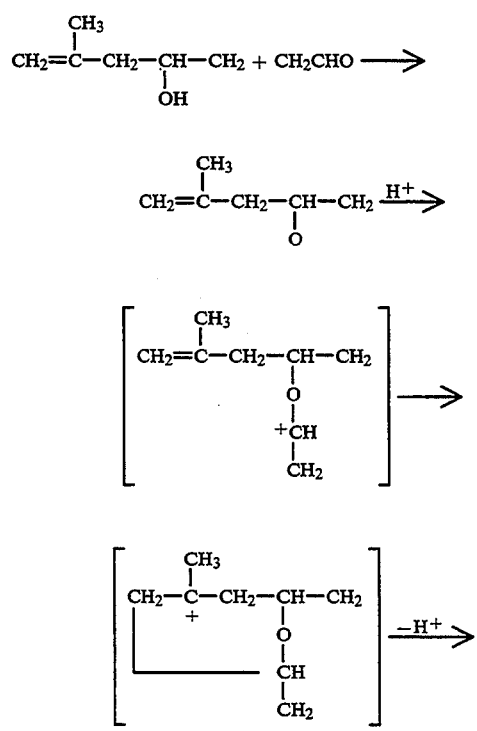

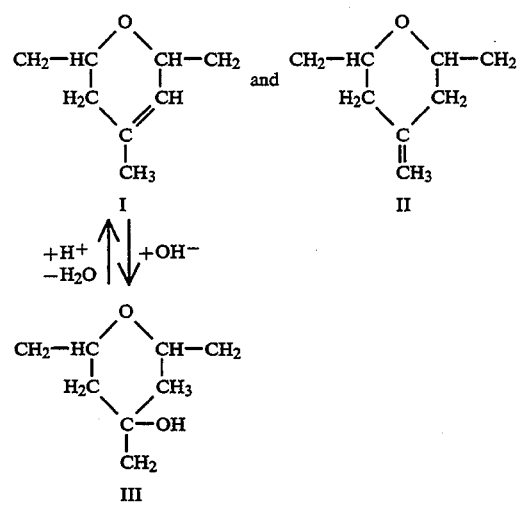

-continued

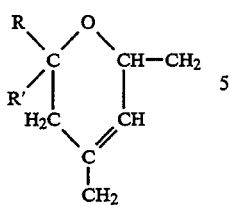

Hinnen, et al, Bull. Soc. Chim. France, 1964 (7), pages 1492-8 discloses the mixture of compounds defined according to the structure:

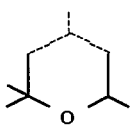

which is in fact a mixture of the compounds, to wit:

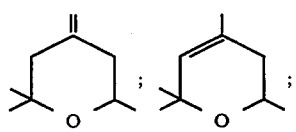

and 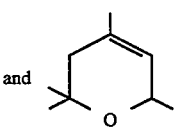

but does not show their organoleptic properties or their usefulness in perfumery. Furthermore, Hinnen, et al does not infer that the mixture of compounds defined according to the structure:

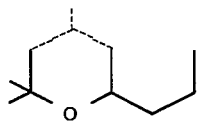

has any useful organoleptic properties or for that matter exists at all.

Hall, et al, U.S. Pat. No. 4,192,782 issued on Jan. 29, 1980 discloses the mixture of compounds defined according to the structure:

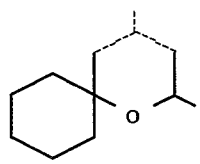

wherein this mixture contains compounds having the structures:

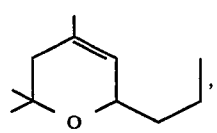

and 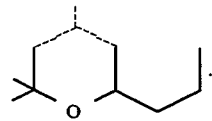

Hall, et al further discloses the perfumery properties of such a mixture, to wit:

"green, herbaceous, sweet, oily, slightly minty aroma with "pickled" green olive topnotes" (column 8, lines 10-15)".

Gramenitakaya, et al, Zh. Org. Khim., 1975, 11(5), pages 990-5 discloses production of the compound having the structure:

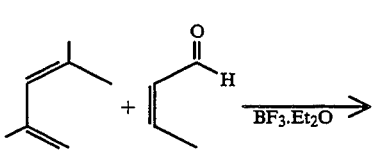

but not the mixture of compounds defined according to the structure:

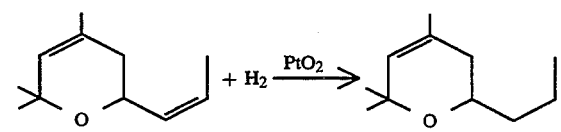

The Gramenitakaya, et al reference discloses the reactions:

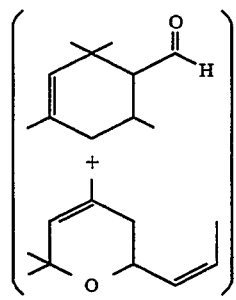

-continued and

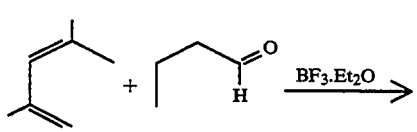

Nothing in the prior art discloses a method for preparation of the genus of compounds defined according to the structure:

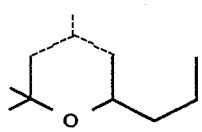

or of the compound having the structure:

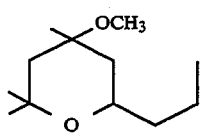

and nothing in the prior art discloses the unexpected, unobvious and advantageous organoleptic properties of the mixture of compounds defined according to the structure:

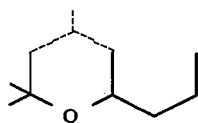

or the compound having the structure:

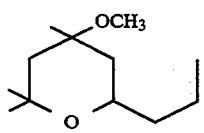

which, in fact, is a mixture of compounds having the structures:

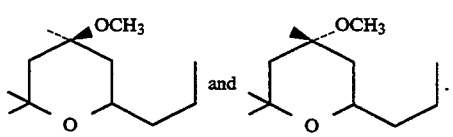

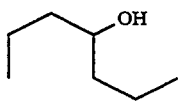

(Conditions: 50 meter×0.32 mm fused silica-methyl silicone column programmed from 75°–225° C. at 2° C. per minute).

Figure 2:
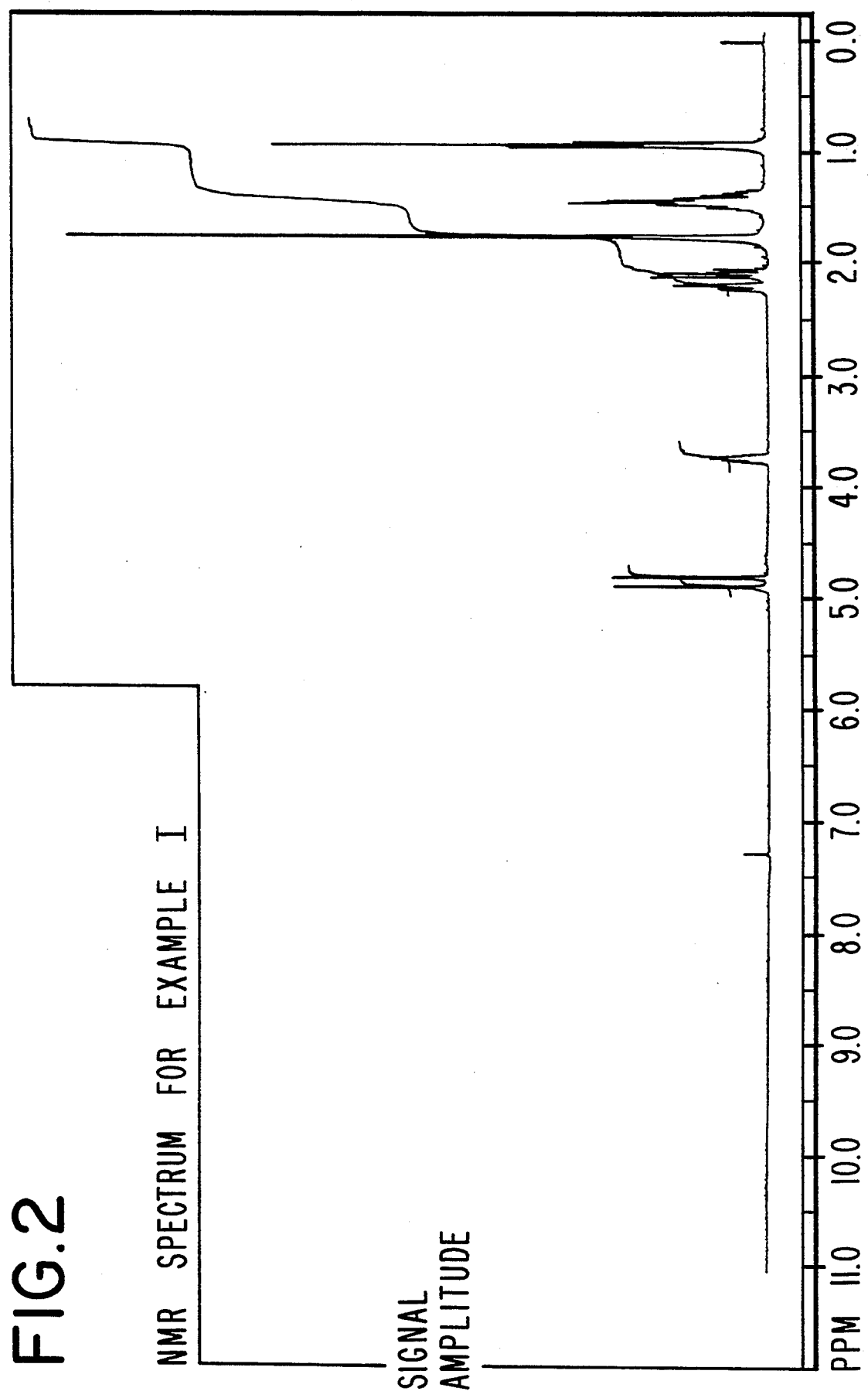

FIG. 2 is the NMR spectrum for the compound having the structure:

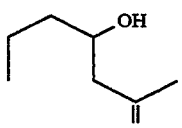

prepared according to Example I.

Figure 3:
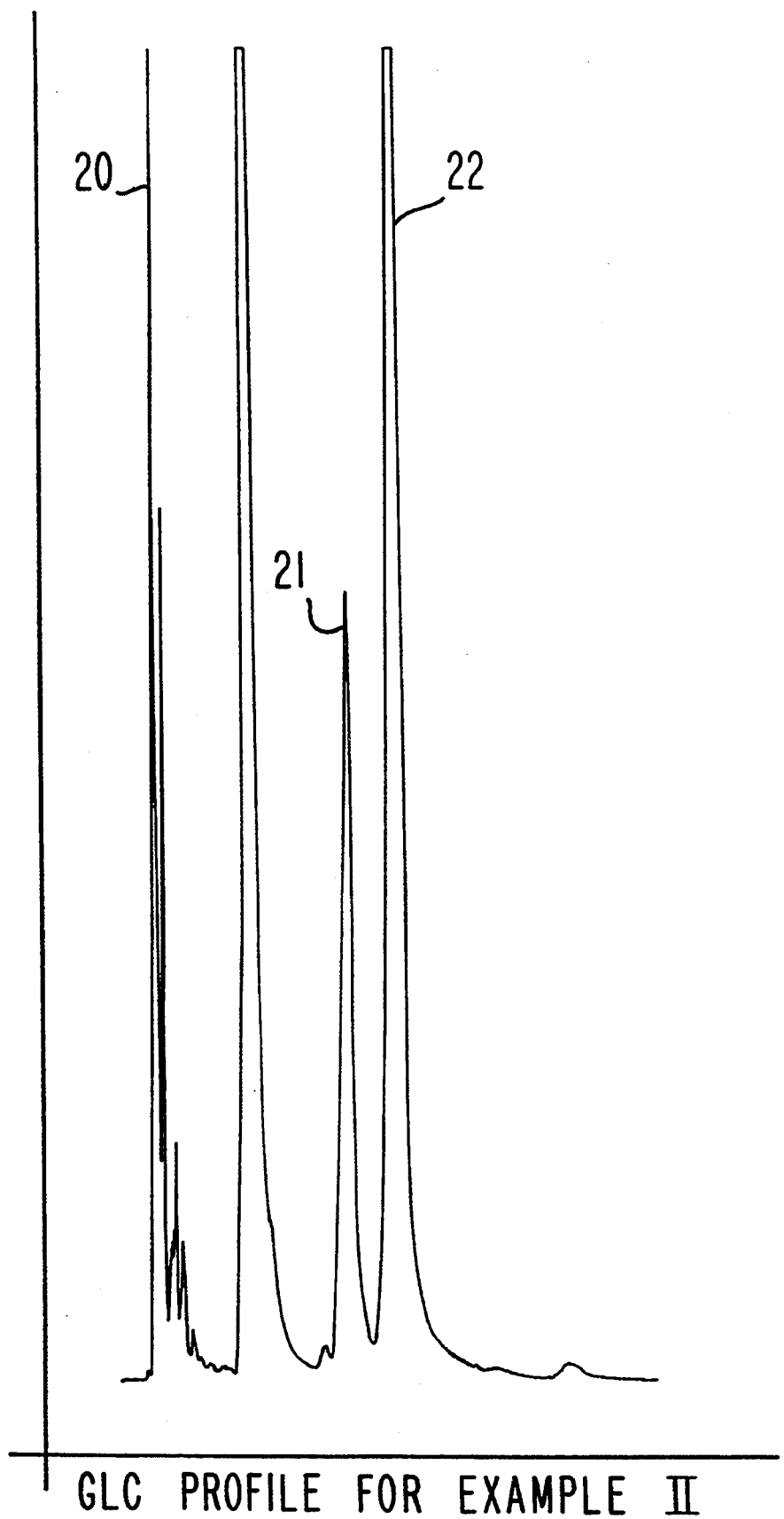

FIG. 3 is the GLC profile for the reaction product of Example II containing the compounds having the structures:

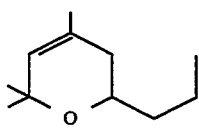

prepared according to Example II (Conditions: SE-30 column programmed at 130° C. isothermal).

Figure 4:
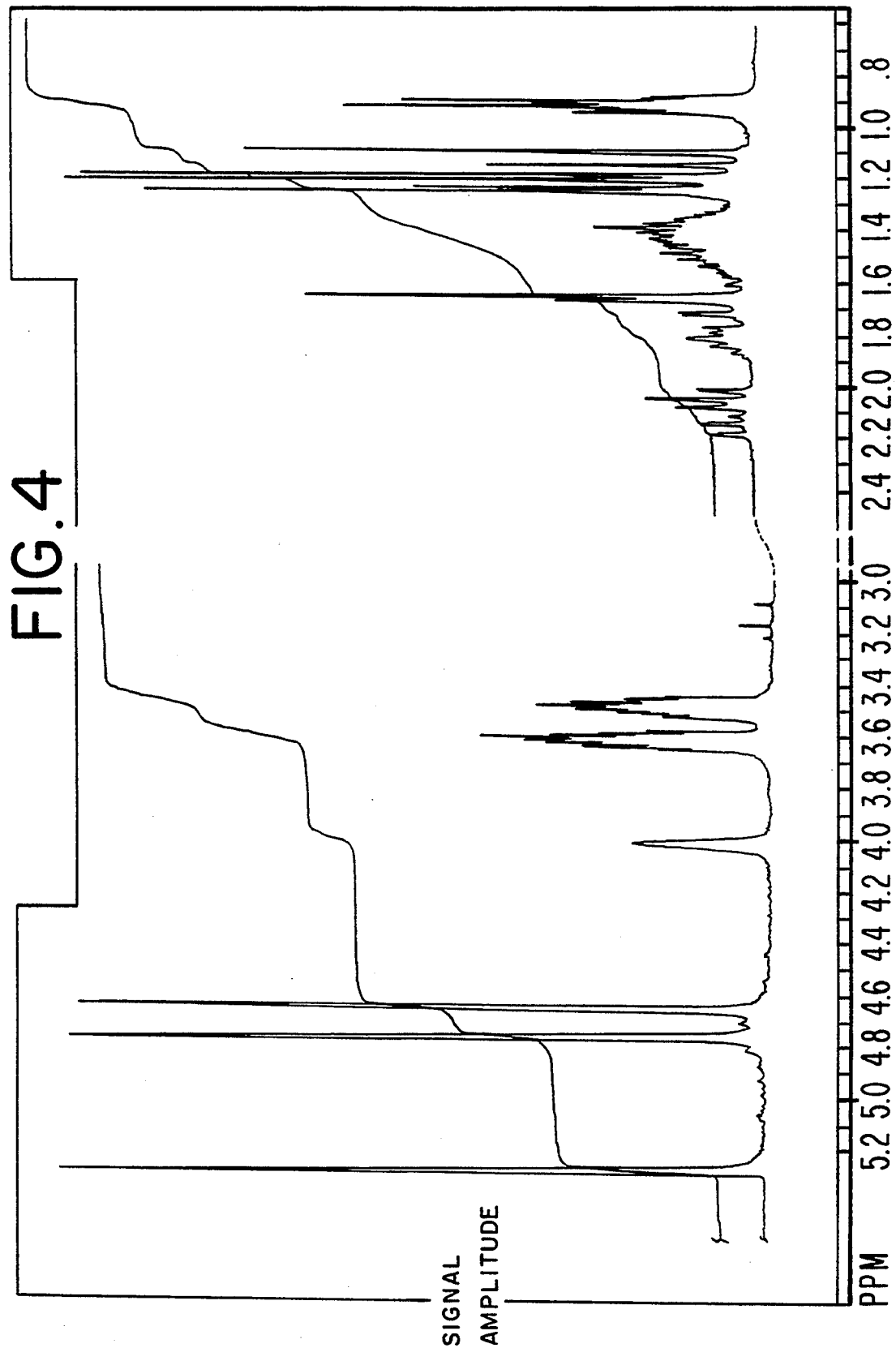

FIG. 4 is the NMR spectrum for the peak indicated by reference numeral 20 of the GLC profile of FIG. 3; for the compounds defined according to the structures:

prepared according to Example II (Conditions: SE-30 column programmed at 130° C. isothermal).

Figure 5:
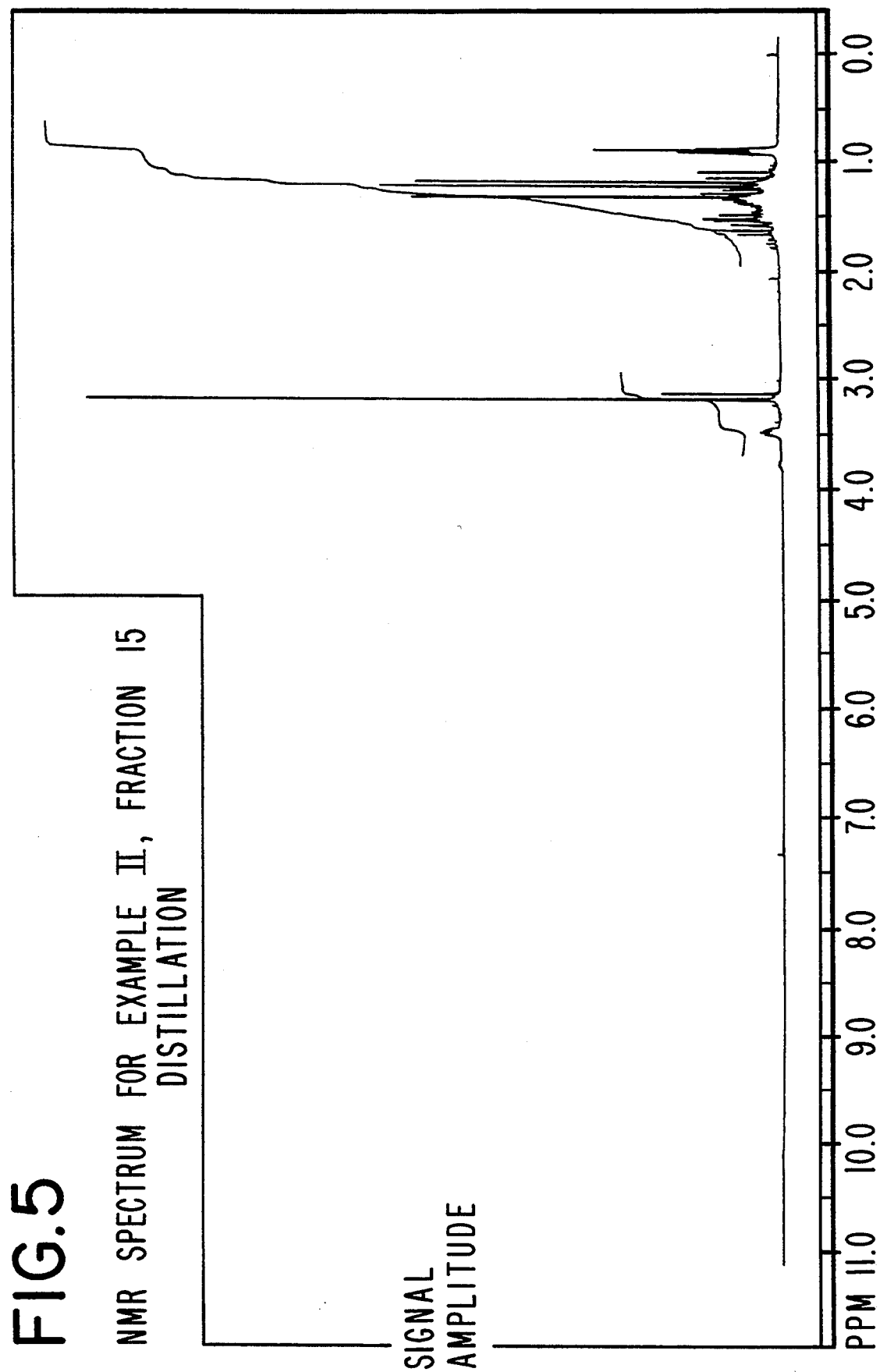

FIG. 5 is the NMR spectrum for distillation Fraction 15 of the distillation product of the reaction product of Example II for the compound having the structure:

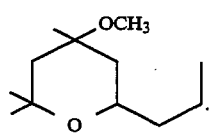

Figures 6, 7:
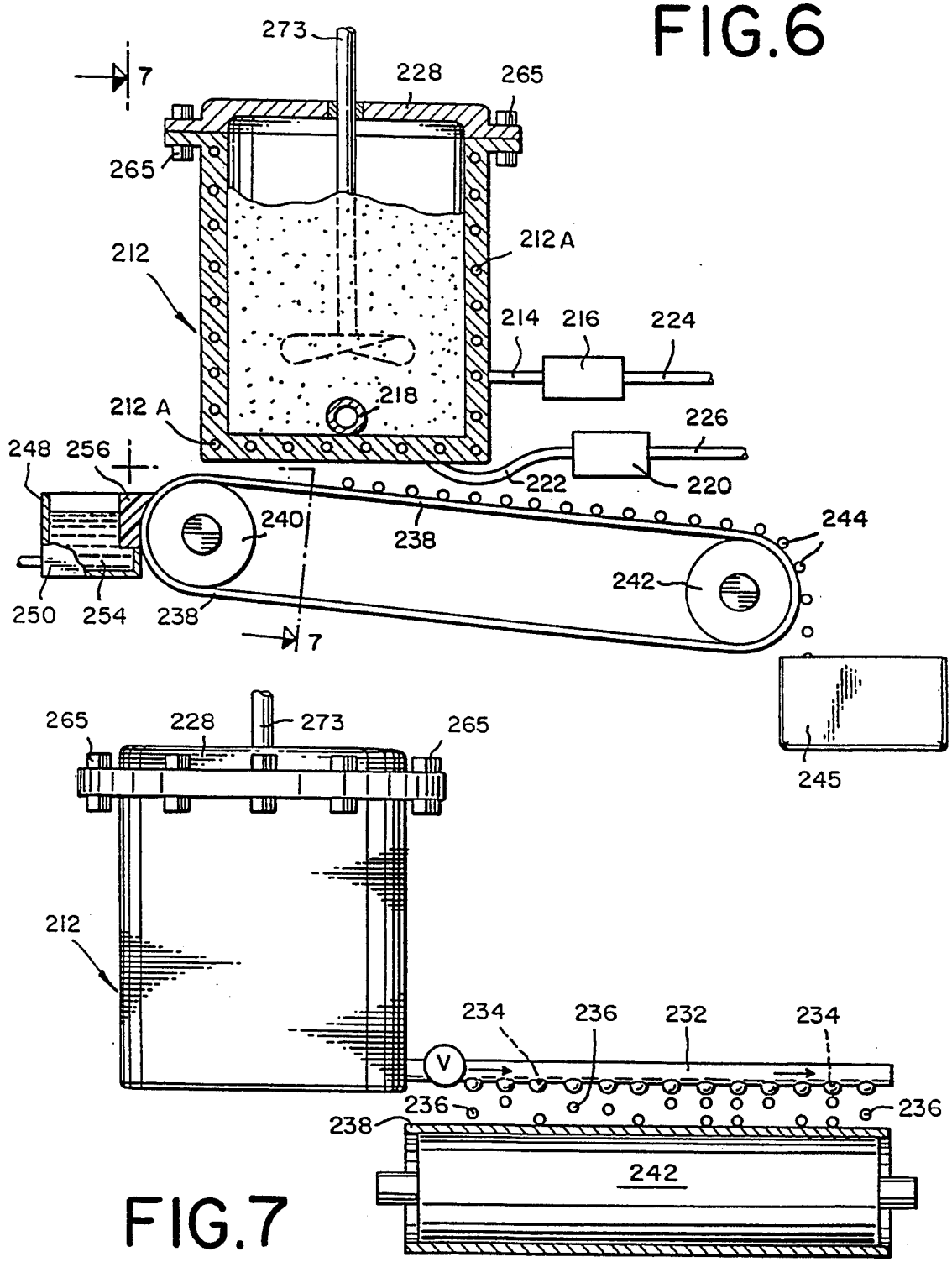

FIG. 6 is a partial side elevation view and partial sectional view of an apparatus for forming polymer pellets containing at least one of the trimethyl and dimethylmethylene propyl polyhydropyran derivatives of our invention.

FIG. 7 is a section taken along line 8—8 of FIG. 6.

DETAILED DESCRIPTION OF THE DRAWINGS

Figure 1:
FIG. 1 is the GLC profile for the reaction product of Example I containing the compound having the structure.

Referring to FIG. 1, FIG. 1 is the GLC profile of the reaction product of Example I. The peak indicated by reference numeral 10 is the peak for tetrahydrofuran solvent. The peak indicated by reference numeral 11 is the peak for toluene solvent. The peak indicated by reference numeral 12 is the peak for the reaction product having the structure:

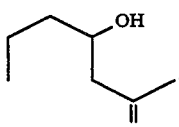

FIG. 3 is the GLC profile for the reaction product of Example II. The peak indicated by reference numeral 20 is the peak for the mixture of compounds defined according to the structure:

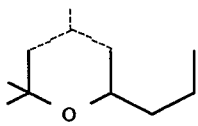

wherein in the mixture, in each of the compounds one of the dashed lines is a carbon-carbon double bond and each of the other of the dashed lines is a carbon-carbon single bond. The peak indicated by reference numeral 20, accordingly, is the peak for the compound mixture for compounds having the structures:

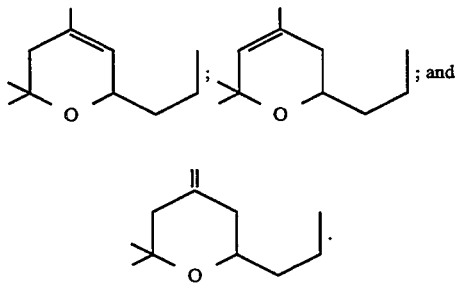

The peak indicated by reference numeral 21 is the peak for the enantiomer of the compound having the structure:

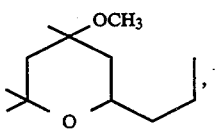

having the structure:

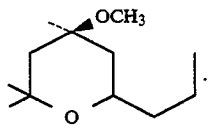

The peak indicated by reference numeral 22 is the peak for the enantiomer of the compound having the structure:

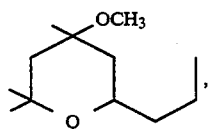

having the structure:

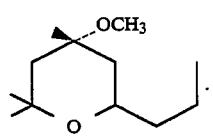

Referring to FIGS. 6 and 7, the apparatus used in producing polymeric fragrances containing one or more of the trimethyl and dimethylmethylene propyl polyhydropyran derivatives of our invention comprises a device for forming scented polyolefin (for example) pellets, which comprises a vat or container 212 into which a mixture of polyolefin such as polyethylene and an aromatic substance or scented material is placed (in this case at least one of the trimethyl and dimethylmethylene propyl polyhydropyran derivatives of our invention).

The container is closed by an air-tight lid 228 in an air-tight manner and is rotated in a suitable manner.

Container 212 having heating coils 212A which are supplied with electric current through cable 224 from a rheostat or control 216 is operated to maintain a temperature inside the container 212 such that polyethylene or other thermoplastic polymer in the container will be maintained in the molten or liquid state. It has been found advantageous to employ a colorless, odorless polymer (e.g., polyethylene) with viscosity ranging between 180 and 220 saybolt seconds and having a melting point in the range of 200°-280° F. The heater 212A is operated to maintain the upper portion of the container 212 within a temperature range of from 250°-350° F. The bottom portion of the container is heated by means of heating coils 212A heated through control 220 connected thereto through a connecting wire 222 to maintain the lower portion of the container within a temperature range of from 250°-350° F.

Thus, polymer (e.g., polyethylene) is added to container 212 and is heated from 10-12 hours whereafter a scented aroma imparting material (at least one of the trimethyl and dimethylmethylene propyl polyhydropyran derivatives of our invention) is added quickly to the melt. The material must be compatible with the polyolefin and forms a homogeneous liquid melt therewith. The scented material is of a type for the particular aroma desired and formulated specifically for the scenting purpose for which the polyolefin will be employed.

Generally, about 5-30% by weight of the scented material (containing at least one of trimethyl and dimethylmethylene propyl polyhydropyran derivatives of our invention) are added to the polyolefin.

After the scent imparting material (e.g., a composition containing at least one of the trimethyl and dimethylmethylene propyl polyhydropyran derivatives of our invention) is added to the container 212, the mixture is stirred for a few minutes, for example, 5-15 minutes, and maintained within the temperature range as indicated, supra, by means of heating coils 212A.

The controls 216 and 220 are connected, respectively, through cables 214 and 222, respectively, to heating coils 212A. The said controls 216 and 220 are also connected through cables 224 and 226, respectively, to a suitable power supply of electric current for supplying the electric power to the heating coils 212A for heating purposes.

Thereafter the valve "V" is opened permitting the mass to flow outwardly through conduit 218/232 having a multiplicity of orifices 234, adjacent to the lower side thereof. The outer end of the conduit 218/232 is closed so that the liquid polymer (e.g., polyolefin) and aroma imparting material (e.g., at least one of the trimethyl and dimethylmethylene propyl polyhydropyran derivatives of our invention) will continuously drop through orifices 234 downwardly from conduit 232. During this time the temperature of the polymer (e.g., polyolefin) and scent imparting material (e.g., a mixture containing at least one of the trimethyl and dimethylmethylene propyl polyhydropyran derivatives of our invention) is accurately controlled so that a temperature in the range of from about 210°-275° F. will exist in the conduit 218/232. The regulation of the temperature through the controls 216 and 220 is essential in order to insure temperature balance to provide for the continuous dropping or dripping of molten polymer (e.g., polyethylene) and scenting material (e.g., one or more of the trimethyl and dimethylmethylene propyl polyhydropyran derivatives of our invention) mixture through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238 they form pellets 244 which harden almost instantaneously and fall off the end of the conveyor 238 into a container 245 and utilized in processes as illustrated, infra.

A feature of this aspect of the process of our invention is the provision for moistening the conveyor belt 238 to insure rapid formation of the solid polymeric (e.g., polyolefin) scented pellets 244 without sticking to the belt. The belt 238 is advantageously fabricated of a material which will not normally stick to a melted plastic but a moistening means 248 insures a sufficiently cold temperature of the belt surface for an adequate formation of the pellets 244. The adequate moistening means comprises a container 250 which is continuously fed with water 254 to maintain a level for moistening a sponge element 256 which bears against the exterior of the belt 238.

THE INVENTION

The present invention provides trimethyl and dimethylmethylene propyl polyhydropyran derivatives defined according to the structure:

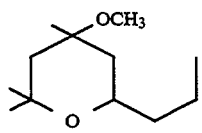

as well as the structure:

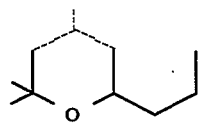

(wherein in the mixture, one of the dashed lines is a carbon-carbon double bond and each of the other of the dashed lines represents a carbon-carbon single bond). Thus, the structure:

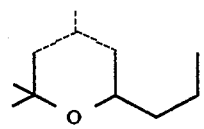

is representative of the mixture of compounds having the structures:

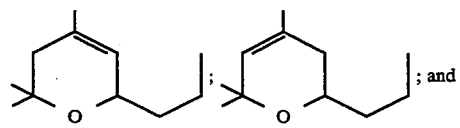

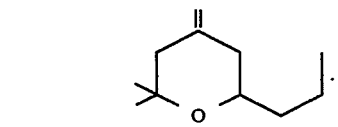

The present invention also provides process intermediates having the structures;

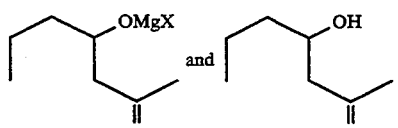

The present invention also provides processes for producing the trimethyl and dimethylmethylene propyl polyhydropyran derivatives of our invention as defined, supra, and for producing the process intermediates as defined, supra.

The trimethyl and dimethylmethylene propyl polyhydropyran derivatives of our invention produced according to the processes of our invention are capable of augmenting, enhancing or providing strong, persistent winey, chamomile, juniper, sage, citrusy, spicy, pineapple, green and floral aromas with natural rose, tobacco-like and animalic undertones to perfume compositions, colognes and perfumed articles (e.g., solid or liquid anionic, cationic, nonionic or zwitterionic detergents, fabric softener articles, drier-added fabric softener articles, fabric softener compositions, cosmetic powders, hair preparations, perfumed polymers and the like).

The substances of our invention are prepared by first reacting a methallyl halide defined according to the structure:

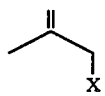

wherein X is chloro or bromo such as methallyl chloride having the structure:

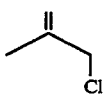

with magnesium in order to form a methallyl magnesium halide having the structure:

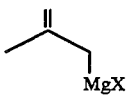

such as methallyl magnesium chloride having the structure:

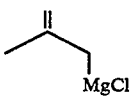

according to the reaction:

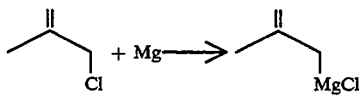

or according to reaction:

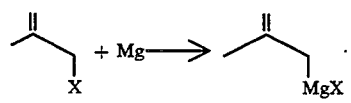

The resulting "Grignard" reagent defined according to the generic structure:

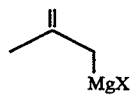

is then reacted with n-butyraldehyde having the structure:

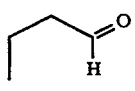

in order to form a magnesium halide salt having the structure:

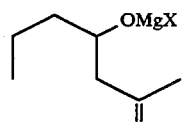

for example, the salt having the structure:

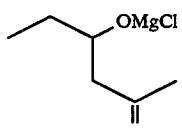

(of our invention ); according to the generic reaction:

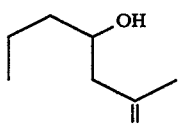

or the specific reaction:

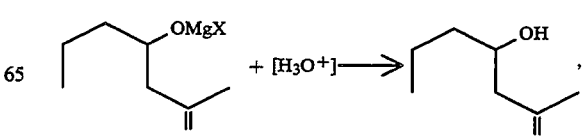

The resulting magnesium halide salt defined according to the structure:

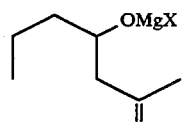

for example, the compound having the structure:

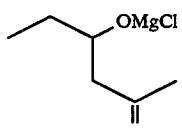

is then hydrolyzed using aqueous acid thereby forming the novel compound having the structure:

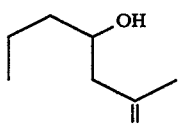

of our invention according to the generic reaction:

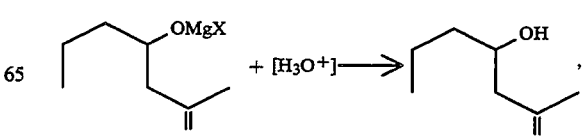

for example, the reaction:

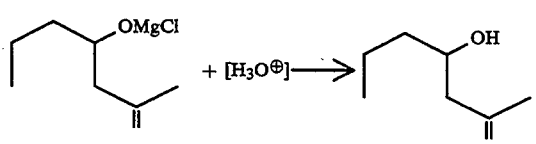

The compound having the structure:

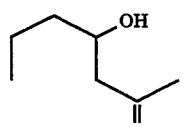

is then reacted with 2,2-dimethoxy propane having the structure:

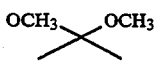

in order to prepare a mixture of compounds having the structures:

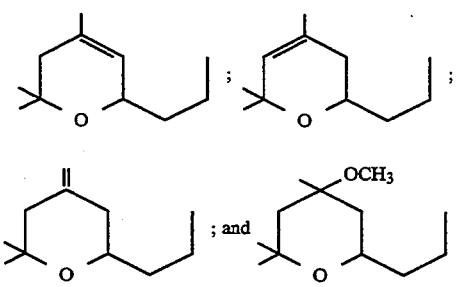

The resulting mixture is then fractionally distilled, the "light" fractions being mixtures of compounds defined according to the structure:

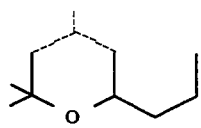

wherein in the mixture, in each of the compounds one of the dashed lines is a carbon-carbon double bond and each of the other of the dashed lines is a carbon-carbon single bond, to wit:

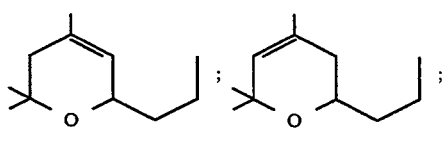

and

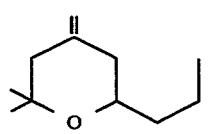

The "heavy" distillation fractions are compounds having the structures:

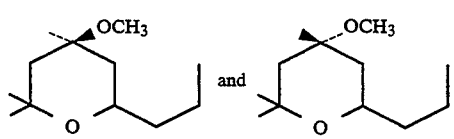

(both being an enantiomer of the compound having the structure:

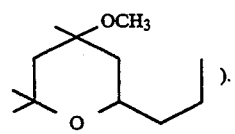

).

More specifically, the reaction:

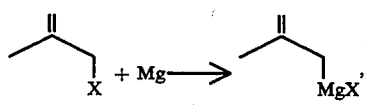

for example, the reaction:

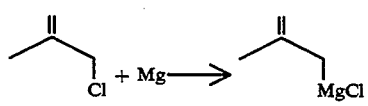

wherein X is chloro or bromo is carried in the presence of either a mixed tetrahydrofuran:toluene solvent (preferably a 50:50 mixture) or a tetrahydrofuran solvent or a mixture of tetrahydrofuran and toluene varying from about 1 part toluene: 50 parts tetrahydrofuran up to about 50 parts toluene: 50 parts tetrahydrofuran. The temperature of reaction varies from about 0° C. up to about 60° C. with a preferred temperature of from about 0° C. up to about 40° C. The resulting product having the structure:

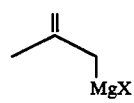

is then, under the same conditions and using the same solvent, reacted with butyraldehyde having the structure:

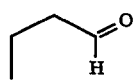

in order to form the resulting magnesium halide salt having the structure:

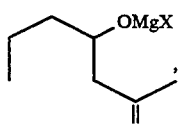

for example, having the structure:

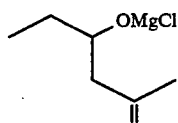

wherein X is chloro or bromo. The resulting product is then hydrolyzed in aqueous acid such as aqueous sulfuric acid, aqueous hydrochloric acid or aqueous ammonium chloride in order to form the novel alcohol of our invention having the structure:

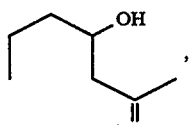

The resulting alcohol having the structure:

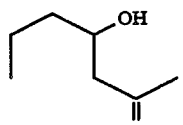

is then fractionally distilled after appropriate "workup" of the reaction mass.

The resulting product having the structure:

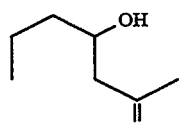

is then reacted with 2,2-dimethoxypropane having the structure:

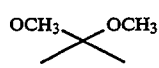

according to the reaction:

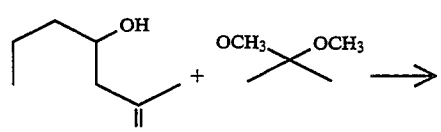

wherein in the structure:

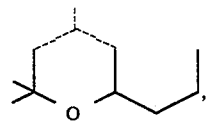

such structure represents a mixture of compounds having the structures:

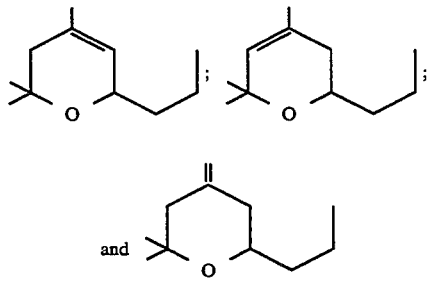

wherein one of the dashed lines represents a carbon-carbon double bond and each of the other of the dashed lines represent carbon-carbon single bonds. This reaction is carried out in the presence of a protonic acid catalyst which may be para-toluene sulfonic acid, concentrated sulfuric acid, xylene sulfonic acid, methane sulfonic acid or phosphoric acid. The temperature of reaction may vary from about 60° C. up to about 80° C. At the end of the reaction, the reaction mass is neutralized, dried and fractionally distilled. The fractional distillation will yield as a "heavy" fraction the compound having the structure:

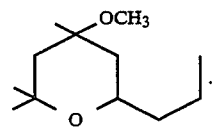

The "light" fractions are mixtures of the compounds having the structures:

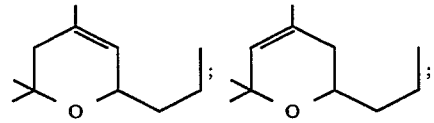

and

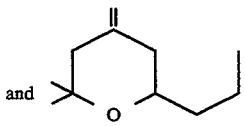

all of which is represented by the structure:

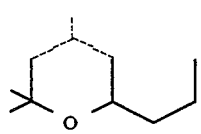

wherein in the mixture, in each of the compounds one of the dashed lines represents a carbon-carbon double bond and each of the other of the dashed lines represent carbon-carbon single bonds.

The following table sets forth the perfumery properties and structures of the materials of our invention:

TABLE I

| Chemical Structure | Perfumery Property |
|---|---|
| The mixture of compounds defined according to the structure: 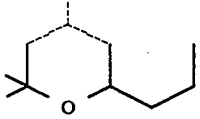 wherein, in each of the compounds one of the dashed lines represents a carbon-carbon double bond and each of the other of the dashed lines represent carbon-carbon single bonds. | A winey, chamomile, juniper, sage, citrusy, spicy, pineapple aroma profile with natural rose, tobacco-like undertones. |
| The compound having the structure: 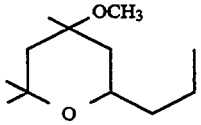 | A green, floral aroma with animalic undertones. |

One or more of the trimethyl and dimethylmethylene propyl polyhydropyran derivatives of our invention prepared in accordance with the process of our invention and one or more auxiliary perfume ingredients including, for example, alcohols, aldehydes, ketches, terpenic hydrocarbons, nitriles, esters, lactones, ethers other than the ethers of our invention, natural essential oils and synthetic essential oils may be admixed so that the combined odors of the individual components produce a pleasant and desired fragrance, particularly and preferably in the floral fragrances. Such compositions usually contain:

(a) the main note or the "bouquet" or foundation stone of the composition;
(b) modifiers which round-off and accompany the main note;
(c) fixatives which include odorous substances which lend a particular note to the perfume throughout all stages of evaporation and substances which retard evaporation; and
(d) topnotes which are usually low boiling, fresh smelling materials.

In perfume compositions, it is the individual components which contribute their particular olfactory characteristics, however, the overall sensory effect of the perfume composition will be at least the sum total of the effects of each of the ingredients. Thus, the trimethyl and dimethylmethylene propyl polyhydropyran derivatives prepared in accordance with the process of our invention can be used to alter, modify or enhance the aroma characteristic of a perfume composition, for example, by utilizing or moderating the olfactory reaction contributed by another ingredient in the composition.

The amount of at least one of the trimethyl and dimethylmethylene propyl polyhydropyran derivatives prepared in accordance with the process of our invention which will be effective in perfume compositions as well as in perfumed articles (e.g., anionic, cationic, nonionic or zwitterionic detergents, soaps, fabric softener compositions, fabric softener articles and perfumed polymers) and colognes depends upon many factors including the other ingredients, their amounts and the effects which are desired. It has been found that perfume compositions containing as little as 0.01% of the trimethyl and dimethylmethylene propyl polyhydropyran derivatives prepared in accordance with the process of our invention or even less (e.g., 0.005%) can be used to impart, augment or enhance strong, persistent, winey, chamomile, juniper, sage, citrusy, spicy, pineapple, green and floral aromas with natural rose, tobacco-like and animalic undertones to soaps, cosmetics, anionic, cationic, nonionic or zwitterionic detergents, fabric softener articles, microporous polymers particularly acrylic resins, polyethylenes and other products. The amount employed can range up to 70% of the fragrance components and will depend on considerations of cost, nature of the end product, the effect desired on the finished product and the particular fragrance sought.

The trimethyl and dimethylmethylene propyl polyhydropyran derivatives of our invention prepared in accordance with the process of our invention are useful (taken alone or together with other ingredients in perfume compositions) as (an)olfactory component(s) in detergents, soaps, space odorants and deodorants, perfumes, colognes, toilet water, bath preparations such as creams deodorants, hand lotions and sun screens; powders, such as talcs, dusting powders, face powders, microporous "perfumed" slow release polymers and the like When used as (an) olfactory component(s) in perfumed articles, as little as 0.005% of the trimethyl and dimethylmethylene propyl polyhydropyran derivatives of our invention prepared in accordance with the process of our invention will suffice to impart, augment or enhance strong, persistent, winey, chamomile, juniper, sage, citrusy, spicy, pineapple, green and floral aromas with natural rose, tobacco-like and animalic undertones. Generally, no more than 6% of the trimethyl and dimethylmethylene propyl polyhydropyran derivatives of our invention based on the ultimate end product is required in the perfumed article. Accordingly, the range of use of the trimethyl and dimethylmethylene propyl polyhydropyran derivatives of our invention in perfumed articles, per se, is from about 0.005% up to about 6% by weight based on the perfumed article.

In addition, the perfume composition or fragrance composition of our invention can contain a vehicle or carrier for one or more of the trimethyl and dimethylmethylene propyl polyhydropyran derivatives of our invention. The vehicle can be a liquid such as a non-toxic alcohol, e.g., ethyl alcohol, a non-toxic glycol, e.g., propylene glycol or the like. The carrier can be an absorbent solid such as a gum (e.g., gum arabic, guar gum or xanthan gum or combinations thereof) or components for encapsulating the composition (such as by coacervanion) or using prepolymers such as urea-formaldehyde prepolymers which are able to form a urea-formaldehyde polymer capsule around a liquid perfume center.

It will thus be apparent that the trimethyl and dimethylmethylene propyl polyhydropyran derivatives of our invention can be utilized to alter, modify or enhance sensory properties particularly organoleptic properties such as fragrances of a wide variety of consumable materials.

The meaning of the term "trimethyl and dimethylmethylene propyl polyhydropyran derivatives of our invention" is intended to cover two materials:

(a) the mixture of compounds having the structure:

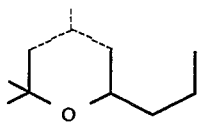

which is a mixture of the compounds:

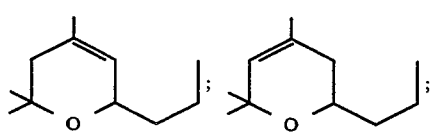

and

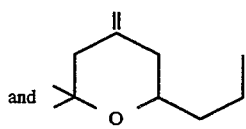

and (b) the compound having the structure:

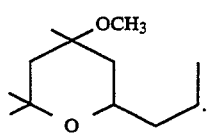

The following Examples I and II set forth means for preparing the trimethyl and dimethylmethylene propyl polyhydropyran derivatives of our invention. The examples including and following Example III, infra, see forth illustrations of organoleptic utilities of the trimethyl and dimethylmethylene propyl polyhydropyran derivatives of our invention.

All parts and percentages given herein are by weight unless otherwise specified.

EXAMPLE I

Preparation of 2-Methyl-1-hepten-4-ol

Reactions:

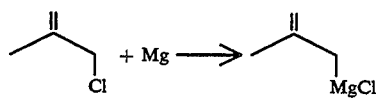

and

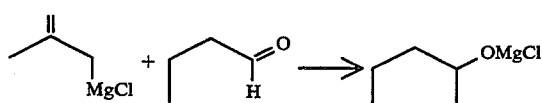

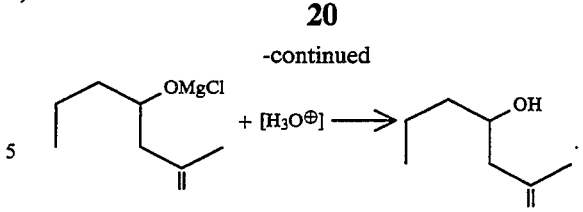

Into a 12 liter flask equipped with stirrer, thermometer, reflux condenser and heating mantle is placed 364.5 grams of magnesium and 1.5 liters of tetrahydrofuran and 2 liters of toluene. With stirring the mixture is heated to 50° C.

During stirring 20 ml methallyl chloride is added to the reaction mass.

Separately, a mixture of 1337.5 grams of methallyl chloride and 1080 grams of butyraldehyde are admixed. The resulting mixture is added, over a period of two hours to the reaction mass while maintaining the reaction mass at 50°-60° C. with stirring.

At the end of the addition of the butyraldehyde/methallyl chloride mixture, the reaction mass is maintained at 50° C. for an additional one hour period.

The reaction mass is then added to a mixture of 8 liters of water and 1020 grams of acetic acid which is maintained at 10° C.

The organic phase is then separated from the aqueous phase and the organic phase is dried over anhydrous magnesium sulfate. The resulting dried organic phase is then distilled on a fractional distillation column yielding the following fractions:

| Fraction No. | Vapor Temp. (°C.) | Liquid Temp. (°C.) | Vacuum mm/Hg. Pressure |
|---|---|---|---|
| 1 | 27/40 | 23/60 | 15.0 |
| 2 | 44 | 70 | 13.0 |
| 3 | 77 | 105 | 11.5 |
| 4 | 85 | 110 | 11.5 |
| 5 | 91 | 99 | 54.0 |
| 6 | 88 | 90 | 45.0 |
| 7 | 75 | 90 | 10.0 |

GCL, NMR, IR and mass spectral analysis yield the information that the resulting compound has the structure:

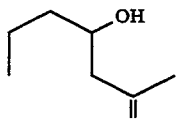

The resulting product is distillation Fraction 7 having a vapor temperature of 75° C. and a liquid temperature of 90° C. at 10 mm/Hg. Fractions 1-6 represent solvent.

EXAMPLE II

Preparation of Trimethyl and Dimethylmethylene Propyl Polyhydropyran Derivatives Reaction:

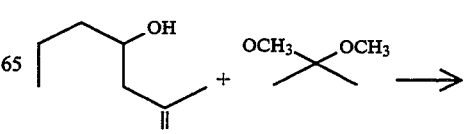

-continued

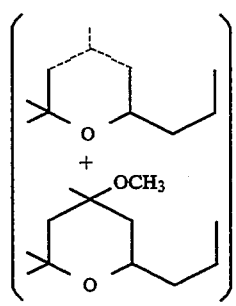

Into a 1 liter reaction vessel equipped with stirrer, thermometer, reflux condenser, heating mantle and addition funnel is placed 312 grams of dimethoxy propane having the structure:

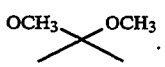

With stirring, the dimethoxy propane is heated to 75° C.

Separately, a mixture of 2-methyl-1-hepten-4-ol (384 grams) is admixed with 6 grams of concentrated (92%) sulfuric acid. The resulting methylheptenol-sulfuric acid mixture (total: 390 grams) is added over a period of two hours to the dimethoxy propane reactant from an addition funnel while maintaining the reaction mass at 75° C.

After completion of the addition of the methylheptenol-sulfuric acid mixture to the dimethoxy propane, the reaction mass was stirred for a period of 15 minutes at 75° C.

The reaction mass was then quenched with 500 ml 10% aqueous sodium hydroxide.

The organic phase is separated from the aqueous phase. The organic phase is dried over anhydrous sodium sulfate and distilled in a fractional distillation column to yield the following fractions:

| Fraction No. | Vapor Temp. (°C.) | Liquid Temp. (°C.) | Vacuum mm/Hg. Pressure |
|---|---|---|---|
| 1 | 23/68 | 23/88 | 10.3/16 |
| 2 | 73 | 92 | 16 |
| 3 | 73 | 92 | 16 |
| 4 | 72 | 92 | 16 |
| 5 | 72 | 93 | 16 |
| 6 | 62 | 95 | 9 |
| 7 | 61 | 95 | 9 |
| 8 | 65 | 88 | 4 |
| 9 | 69 | 88 | 4 |
| 10 | 70 | 93 | 4 |
| 11 | 71 | 88 | 4 |
| 12 | 71 | 88 | 4 |
| 13 | 75 | 98 | 4 |
| 14 | 75 | 98 | 4 |
| 15 | 75 | 99 | 4 |
| 16 | 75 | 108 | 3.4 |
| 17 | 76 | 170 | 3.5 |
| 18 | 32 | 180 | 3.5. |

Fractions 2-9 are bulked. NMR, IR and mass spectral analysis yield the information that bulked Fractions 2-9 is a mixture of the compounds:

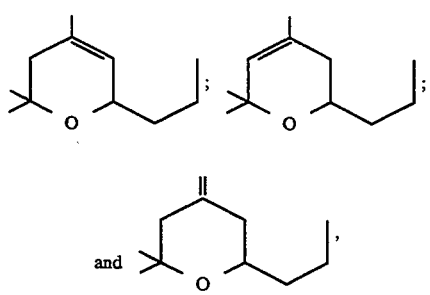

defined according to the structure:

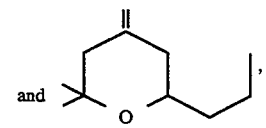

wherein in the mixture, in each of the compounds one of the dashed lines is a carbon-carbon double bond and each of the other of the dashed lines represents a carbon-carbon single bond.

Fractions 10–18 are bulked and bulked Fractions 10 and 18 are confirmed by NMR, IR and mass spectral analysis to be the compound having the structure:

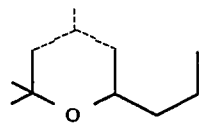

with its enantiomers having the structures:

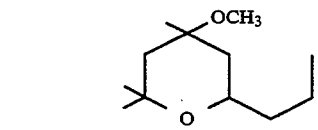

The mixture of compounds defined according to the structure:

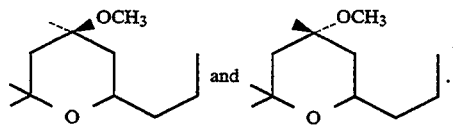

has a winey, chamomile, juniper, sage, citrusy, spicy and pineapple aroma profile with natural rose, tobacco-like undertones.

The compound having the structure:

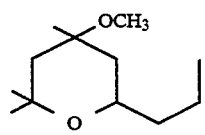

has a green floral aroma with animalic undertones.

EXAMPLE III

Perfume Formulations

The following woody, floral cologne perfume formulations are prepared:

| Ingredients | Parts by Weight | | |
|---|---|---|---|
| | Example III(A) | Example III(B) | Example III(C) |
| Bergamot oil | 150 | 150 | 150 |
| Orange oil | 200 | 200 | 200 |
| Lemon oil | 50 | 50 | 50 |
| Eugenol | 10 | 10 | 10 |
| 4-(4-Methyl-4-hydroxy amyl)-Delta³cyclohexene carboxaldehyde (LYRAL ® Trademark of International Flavors & Fragrances Inc. of New York, New York) | 40 | 40 | 40 |
| Ylang oil | 2 | 2 | 2 |
| Petigrain Paraguay | 10 | 10 | 10 |
| Gamma-Methyl ionone | 20 | 20 | 20 |
| Vetiver Venezuela | 18 | 18 | 18 |
| 3-Alpha-methyl-dodecahydro-6,6,9a-trimethyl-napthol[2,1-b]furan; product produced by the reaction of acetic anhydride, polyphosphoric acid and 1,5,9-trimethyl cyclododecatriene-1,5,9-according to the process of Example I of U.S. Letters Pat. No. 3,718,698, the specification for which is incorporated herein by reference | 50 | 50 | 50 |
| Octahydro-9,9-dimethyl-1,6-methanonaphthalene-1-[2H]-ol produced according to Example III of U.S. Letters Pat. No. 3,996,169, the specification for which is incorporated by reference herein | 50 | 50 | 50 |
| The mixture of compounds defined according to the structure: 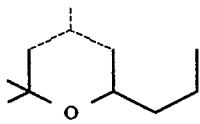 wherein in the mixture, in each of the compounds one of the dashed lines is a carbon-carbon double bond and each of the other of the dashed lines is a carbon-carbon single bond produced according to Example II, bulked distillation Fractions 2-9, supra. | 12 | 0 | 0 |
| The compound having the structure: 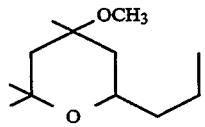 prepared according to Example II, supra, bulked distillation Fractions 10-18. | 0 | 12 | 0 |
| Mixture of the compounds defined according to the structure: 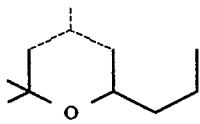 prepared according to Example II, bulked distillation Fractions 2-9 and the compound having the structure: 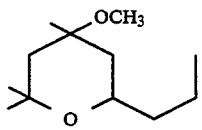 produced according to Example II, bulked distillation Fractions 10-18. | 0 | 0 | 12 |

The mixture of compounds having the structure:

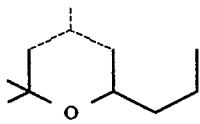

prepared according to Example II, bulked distillation Fractions 2-9 imparts to this woody, floral cologne perfume formulation winey, chamomile, juniper, sage, citrusy, spicy and pineapple topnotes with natural rose and tobacco-like undertones. Accordingly, the perfume composition of Example III(A) can be described as "a woody, floral, cologne aroma with winey, chamomile, juniper, sage, citrusy, spicy, pineapple topnotes and with natural rose and tobacco-like undertones".

The compound having the structure:

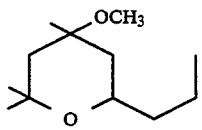

prepared according to Example II, bulked distillation Fractions 10-18 imparts to this woody, floral cologne perfume formulation green topnotes and animalic undertones. Accordingly, the perfume composition of Example III(B) can be described as "a woody, floral and cologne aroma with green topnotes and animalic undertones".

The mixture of compounds defined according to the structures:

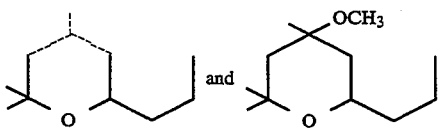

prepared according to Example II imparts to this woody, floral and cologne perfume formulation winey, chamomile, juniper, sage, citrusy, spicy, pineapple, green and floral topnotes with natural rose, tobacco-like and animalic undertones. Accordingly, the perfume composition of Example III(C) can be described as "a woody, floral and cologne aroma with winey, chamomile, juniper, sage, citrusy, spicy, pineapple, green and floral topnotes and with natural rose, tobacco-like and animalic undertones".

EXAMPLE IV

Preparation of Cosmetic Powder Composition

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
|---|---|
| The mixture of compounds defined according to the structure: <br><br> wherein in the mixture, in each of the compounds one of the dashed lines is a carbon-carbon double bond and each of the other of the dashed lines is a carbon-carbon single bond produced according to Example II, bulked distillation Fractions 2-9. | A winey, chamomile, juniper, sage, citrusy, spicy, pineapple aroma profile with natural rose and tobacco-like undertones. |
| The compound having the structure: 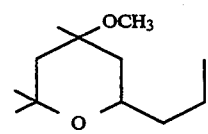 <br> prepared according to Example II, bulked distillation Fractions 10-18. | A green, floral aroma with animalic undertones. |
| The perfume composition of Example III(A). | A woody, floral cologne aroma with winey, chamomile, juniper, sage, citrusy, spicy, pineapple topnotes and with natural rose and tobacco-like undertones. |
| The perfume composition of Example III(B). | A woody, floral and cologne aroma with green topnotes and animalic undertones. |
| The perfume composition of Example III(C). | A woody, floral and cologne aroma with winey, chamomile, juniper, sage, citrusy, spicy, pineapple, green and floral topnotes and with natural rose, tobacco-like and animalic |

TABLE II-continued

| Substance | Aroma Description |
|---|---|
| | undertones. |

EXAMPLE V

Perfumed Liquid Detergents

Concentrated liquid detergents (Lysine sale of n-dodecyl-benzene sulfonic acid as more specifically described in U.S. Pat. No. 3,948,818 issued on Apr. 6, 1976 incorporated by reference herein) with aroma nuances as set forth in Table II of Example IV are prepared containing 0.10%, 0.15%, 0.20, 0.25%, 0.30% and 0.35% of the substance set forth in Table II of Example IV. They are prepared by adding and homogeneously mixing the appropriate quantity of substance set forth in Table II of Example IV in the liquid detergent. The detergents all possess excellent aromas as set forth in Table II of Example IV, the intensity increasing with greater concentrations of substances as set forth in Table II of Example IV.

EXAMPLE VI

Preparation of Colognes and Handkerchief Perfumes

Compositions as set forth in Table II of Example IV are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example IV are imparted to the colognes and to the handkerchief perfumes at all levels indicated.

EXAMPLE VII

Preparation of Soap Compositions

One hundred grams of soap chips [per sample] (IVORY ®, produced by the Procter & Gamble Company of Cincinnati, Ohio), are each mixed with one gram samples of substances as set forth in Table II of Example IV until homogeneous compositions are obtained. In each of the cases, the homogeneous compositions are heated under 8 atmospheres pressure at 180° C. for a period of three hours and the resulting liquids are placed into soap molds. The resulting soap cakes, on cooling manifest aromas as set forth in Table II of Example IV.

EXAMPLE VIII

Preparation of Solid Detergent Compositions

Detergents are prepared using the following ingredients according to Example I of Canadian Patent No. 1,007,948 (incorporated by reference herein):

| Ingredient | Percent by Weight |
|---|---|
| "Neodol ®" 45-11 (a $C_{12}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

The detergent is a phosphate-free detergent. Samples of 100 grams each of this detergent are admixed with 0.10, 0.15, 0.20 and 0.25 grams of each of the substances as set forth in Table II of Example IV. Each of the detergent samples has an excellent aroma as indicated in Table II of Example IV.

EXAMPLE IX

Utilizing the procedure of Example I at column 15 of U.S. Pat. No. 3,632,396 (the disclosure of which is incorporated herein by reference), non-woven cloth substrates useful as drier-added fabric softening articles of manufacture are prepared wherein the substrate, the substrate coating, the outer coating and their perfuming material are as follows:
1. A water "dissolvable" paper ("Dissolvo Paper");
2. Adogen 448 (m.p. about 140° F.) as the substrate coating; and
3. An outer coating having the following formulation (m.p. about 150° F.):
  57%—$C_{20-22}$ HAPS;
  22%—isopropyl alcohol;
  20%—antistatic agent; and
  1%—of one of the substances as set forth in Table II of Example IV.

Fabric softening compositions prepared according to Example I at column 15 of U.S. Pat. No. 3,632,396 having the aroma characteristics as set forth in Table II of Example IV, supra, consist of a substrate coating having a weight of about 3 grams per 100 square inches of substrate, a first coating located directly on the substrate coating consisting of about 1.85 grams per 100 square inches of substrate; and an outer coating coated on the first coating consisting of about 1.4 grams per 100 square inches of substrate. One of the substances of Table II of Example IV is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table II of Example IV, supra.

EXAMPLE X

Hair Spray Formulations

The following hair spray formulation is prepared by first dissolving PVP/VA E-735 copolymer manufactured by the GAF Corporation of 140 West 51st Street, New York, N.Y., in 91.62 grams of 95% of food grade ethanol. 8.0 Grams of the polymer is dissolved in the alcohol. The following ingredients are added to the PVP/VA alcoholic solution:

| Ingredient | Percent by Weight |
| --- | --- |
| Dioctyl sebacate | 0.05 |
| Benzyl alcohol | 0.10 |
| Dow Corning 473 fluid (prepared by the Dow Corning Corporation) | 0.10 |
| TWEEN ® 20 surfactant (prepared by ICI America Corporation) | 0.03 |
| One of the perfumery substances as set forth in Table II of Example IV, supra. | 0.10 |

The perfuming substances as set forth in Table II of Example IV add aroma characteristics as set forth in Table II of Example IV which are rather intense and aesthetically pleasing to the users of the soft-feel, good-hold pump hair sprays.

EXAMPLE XI

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stephan Chemical Company (35.0 weight percent). The resulting mixture is heated to 60° C. and mixed until a clear solution is obtained (at 60° C.). This material is "COMPOSITION A".

GAFQUAT ® 755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "COMPOSITION B".

The resulting "COMPOSITION A" and "COMPOSITION B" are then mixed in a 50:50 weight ratio of A:B and cooled to 45° C. and 0.3 weight percent of perfuming substance as set forth in Table II of Example IV is added to the mixture. The resulting mixture is cooled to 40° C. and blending is carried out for an additional one hour in each case. At the end of this blending period, the resulting material has a pleasant fragrance as indicated in Table II of Example IV.

What is claimed is:

1. The compound having the structure:

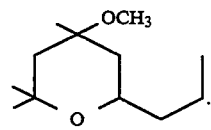

2. The mixture of compounds having the structures:

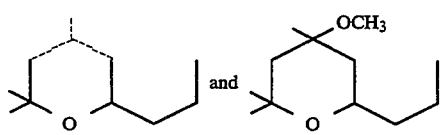

wherein in the mixture defined according to the structure:

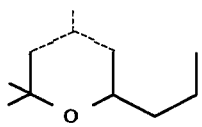

in each of the compounds of the mixture one of the dashed lines represents a carbon-carbon double bond and each of the other of the dashed lines represents a carbon-carbon single bond.

3. A process for augmenting, enhancing or imparting an aroma in or to a consumable material selected from the group consisting of perfume compositions, colognes or perfumed articles comprising the step of intimately admixing with said perfume composition, cologne or perfumed article, an aroma imparting, augmenting or enhancing quantity of a composition of matter defined according to claim 1.

4. A process for augmenting, enhancing or imparting an aroma in or to a consumable material selected from the group consisting of perfume compositions, colognes or perfumed articles comprising the step of intimately admixing with said perfume composition, cologne or perfumed article, an aroma imparting, augmenting or enhancing quantity of a composition of matter defined according to claim 2.

5. A perfume composition comprising a perfume base and intimately admixed therewith an aroma augmenting, enhancing or imparting quantity of a composition of matter defined according to claim 1.

6. A perfume composition comprising a perfume base and intimately admixed therewith an aroma augmenting, enhancing or imparting quantity of a composition of matter defined according to claim 2.

7. A perfumed article comprising a perfumed article base an intimately admixed therewith an aroma augmenting, enhancing or imparting quantity of a composition of matter defined according to claim 1.

8. A perfumed article comprising a perfumed article base an intimately admixed therewith an aroma augmenting, enhancing or imparting quantity of a composition of matter defined according to claim 2.

9. A cologne comprising water, ethyl alcohol and an aroma imparting quantity of a composition of matter defined according to claim 1.

10. A cologne comprising water, ethyl alcohol and an aroma imparting quantity of a composition of matter defined according to claim 2.

11. A perfumed polymer comprising a microporous polymer and having contained in the interstices thereof an aroma imparting quantity of a composition of matter defined according to claim 1.

12. A perfumed polymer comprising a microporous polymer and having contained in the interstices thereof an aroma imparting quantity of a composition of matter defined according to claim 2.

* * * * *